(12) United States Patent
Tanaka et al.

(10) Patent No.: US 10,391,205 B2
(45) Date of Patent: Aug. 27, 2019

(54) POLYMER FOR MEDICAL DEVICE, MEDICAL DEVICE MATERIAL AND MEDICAL DEVICE PREPARED FROM THE MATERIAL, AND MONOMER COMPOSITION FOR POLYMER FOR USE IN PRODUCTION OF MEDICAL DEVICE

(71) Applicants: National University Corporation Yamagata University, Yamagata-shi, Yamagata (JP); NIPPON SHOKUBAI CO., LTD., Osaka-shi, Osaka (JP)

(72) Inventors: Masaru Tanaka, Yamagata (JP); Naoki Kobayashi, Osaka (JP); Yoshitomo Nakata, Osaka (JP); Asuka Sugawara, Osaka (JP)

(73) Assignees: National University Corporation Yamagata University, Yamagata (JP); Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 15/362,322

(22) Filed: Nov. 28, 2016

(65) Prior Publication Data

US 2017/0157304 A1 Jun. 8, 2017

(30) Foreign Application Priority Data

Dec. 2, 2015 (JP) ................................. 2015-236069

(51) Int. Cl.
| | |
|---|---|
| *C08F 220/12* | (2006.01) |
| *C08F 220/18* | (2006.01) |
| *A61L 33/06* | (2006.01) |
| *C08F 220/28* | (2006.01) |

(52) U.S. Cl.
CPC .......... *A61L 33/064* (2013.01); *C08F 220/12* (2013.01); *C08F 220/18* (2013.01); *C08F 220/28* (2013.01); *C08F 2220/282* (2013.01)

(58) Field of Classification Search
None
See application file for complete search history.

(56) References Cited

U.S. PATENT DOCUMENTS

| | | | | |
|---|---|---|---|---|
| 6,653,426 | B2 * | 11/2003 | Alvarado | A61K 9/0024 526/319 |
| 2004/0170752 | A1 * | 9/2004 | Luthra | A61L 31/10 427/2.24 |
| 2006/0105099 | A1 * | 5/2006 | Takahashi | C09D 5/1668 427/2.1 |
| 2017/0157304 | A1 * | 6/2017 | Tanaka | A61L 33/064 |

FOREIGN PATENT DOCUMENTS

| | | |
|---|---|---|
| JP | 5-310867 | 11/1993 |
| JP | 7-016292 | 1/1995 |
| JP | 2002-356519 | 12/2002 |
| JP | 2005-232237 | 9/2005 |
| JP | 2006-158961 | 6/2006 |
| JP | 2006-519049 | 8/2006 |
| WO | 2004/075943 | 9/2004 |

* cited by examiner

*Primary Examiner* — Peter A Salamon
(74) *Attorney, Agent, or Firm* — Hamre, Schumann, Mueller & Larson, P.C.

(57) ABSTRACT

To Provide is a polymer having high antithrombogenicity compared to a conventional polymer having a glycerol group and suitable as a medical device material. It is the polymer having a structural unit derived from a glycerol group-containing monomer, and a structural unit derived from an unsaturated monomer having a structure in which an organic group having a structure site having 4 or more carbon atoms continuously bound is bound to an ethylenically unsaturated group; and satisfying a glass-transition temperature of 10° C. or less and/or a glass-transition temperature of −25° C. or less at a saturated water content.

20 Claims, No Drawings

POLYMER FOR MEDICAL DEVICE, MEDICAL DEVICE MATERIAL AND MEDICAL DEVICE PREPARED FROM THE MATERIAL, AND MONOMER COMPOSITION FOR POLYMER FOR USE IN PRODUCTION OF MEDICAL DEVICE

TECHNICAL FIELD

The present invention relates to a polymer for a medical device and others, and more specifically, e.g., a polymer for a medical device suitable as a medical device material to be used in contact with a biogenic substance or a body tissue and having high biocompatibility and a monomer composition for a polymer for use in producing a medical device as a starting composition.

BACKGROUND ART

A polymer compound can be designed so as to have various characteristics by selecting a monomer as a starting material and is employed in a wide variety of uses from industrial products to daily commodities. Use in a medical device is one of the uses of a polymer compound. A medical device is used in an environment where it comes into contact with a biogenic substance such as blood and a body tissue. If the surface of a medical device has a low affinity for a biogenic substance and a body tissue, a biological defense mechanism is activated to coagulate blood, with the result that a problem such as formation of thrombus occurs. Because of this, at least the surface of a medical device to be in contact with a biological component and a body tissue must be formed of a highly biocompatible material.

As the polymer compound to be used for a medical device, conventionally, 2-(methacryloyloxy)ethyl-2'-(trimethylammonio)ethyl phosphate (MPC) polymer (PMPC), a polymer having a betaine structure and a methoxyethyl acrylate polymer (PMEA), are known. However, PMPC and the polymer having a betaine structure are expensive and highly hygroscopic. Both have a problem in handling. PMEA cannot be said to have sufficient substrate adhesion.

Because of these problems, investigation has been further conducted on materials. Literatures disclose an article for a bio-related substance having a surface film, which is formed by bringing a coating composition for preventing adsorption of a bio-related substance, containing a copolymer obtained from a starting monomer containing two types of specific monomers, a cross-linking agent and a solvent, into contact with the surface, followed by heating (see, Patent Literature 1); an antithrombogenic material for medical equipment, formed of a graft copolymer obtained by graft polymerization of a specific radical polymerizable monomer to a thermoplastic elastomer (see, Patent Literature 2); a phosphorylcholine analogous group-containing polymer obtained from e.g., a phosphorylcholine analogous group-containing monomer as a starting material (see, Patent Literature 3); and a method for forming a layer of a therapeutic drug-containing composition bound to a specific copolymer, on therapeutic agent delivery medical equipment (see, Patent Literature 4). Other literatures also disclose various copolymers having a structure unit derived from glycerol mono(meth)acrylate (see, Patent Literatures 5 and 6).

CITATION LIST

Patent Literature

Patent Literature 1: JP 2006-158961 A
Patent Literature 2: JP 7-16292 A
Patent Literature 3: JP 2002-356519 A
Patent Literature 4: JP 2006-519049 T
Patent Literature 5: JP 2005-232237 A
Patent Literature 6: JP 5-310867 A

SUMMARY OF INVENTION

Technical Problem

In the aforementioned literatures, a polymer having a glycerol group is used as a polymer material; however, it cannot be said that antithrombogenicity of them is sufficient. As a polymer for a medical device, there is room for designing/developing a polymer having a more suitable performance.

The present invention was attained in consideration of the aforementioned circumstances. An object of the invention is to provide a polymer having higher antithrombogenicity than a conventional polymer having a glycerol group and more suitable as a medical device material.

Solution to Problem

The present inventors conducted various studies on a polymer having higher antithrombogenicity than a conventional polymer having a glycerol group. As a result, they found that a polymer having a structural unit derived from a glycerol group-containing monomer and a structural unit derived from an unsaturated monomer having a structure in which an organic group having a structure site having 4 or more carbon atoms continuously bound is bound to an ethylenically unsaturated group, and satisfying at least one of a glass-transition temperature being 10° C. or less and a glass-transition temperature being −25° C. or less at a saturated water content; and a polymer having a glycerol group in a ratio of 1 mmol or more per 1 g of polymer and satisfying at least one of a glass-transition temperature being 10° C. or less and a glass-transition temperature being −25° C. or less at a saturated water content, have higher antithrombogenicity than a conventional polymer having a glycerol group, and sufficiently suppress adhesion and activation of platelet cells, and thus, are more suitable polymers as a medical device material.

More specifically, the present invention relates to the polymer to be used as a material for a medical device, having a structural unit derived from a glycerol group-containing monomer and a structural unit derived from an unsaturated monomer having a structure in which an organic group having a structure site having 4 or more carbon atoms continuously bound is bound to an ethylenically unsaturated group; and satisfying a glass-transition temperature of 10° C. or less and/or a glass-transition temperature of −25° C. or less at a saturated water content.

The present invention also relates to the polymer to be used as a material for a medical device, having a glycerol group in a ratio of 1 mmol or more per 1 g of polymer and satisfying a glass-transition temperature of 10° C. or less and/or a glass-transition temperature of −25° C. or less at a saturated water content.

Advantageous Effects of Invention

The polymer for a medical device of the present invention is constituted as mentioned above, has excellent antithrombogenicity and sufficiently suppresses adhesion and activation of platelets. Because of this, the polymer of the invention can be suitably used as e.g., a material for a medical device and an antithrombogenic coating agent.

DESCRIPTION OF EMBODIMENTS

Now, the present invention will be more specifically described below.

Note that, a combination of two or more preferred embodiments of the present invention described below is also regarded as a preferred embodiment of the present invention.

As the polymer for a medical device of the present invention, there are two polymers:

(1) having a structural unit derived from a glycerol group-containing monomer and a structural unit derived from an unsaturated monomer having a structure in which an organic group having a structure site having 4 or more carbon atoms continuously bound is bound to an ethylenically unsaturated group; and satisfying a glass-transition temperature of 10° C. or less and/or a glass-transition temperature of −25° C. or less at a saturated water content; and (2) having a glycerol group in a ratio of 1 mmol or more per 1 g of polymer and satisfying a glass-transition temperature of 10° C. or less and/or a glass-transition temperature of −25° C. or less at a saturated water content. Both polymers are characterized in that each of the glass-transition temperature and/or the glass-transition temperature at a saturated water content fall within a predetermined temperature or less.

Hereinafter, the polymer for a medical device according to (1) will be referred to as "the polymer for a medical device of a first invention"; and the polymer for a medical device according to (2) will be referred to as "the polymer for a medical device of a second invention". Further, a polymer for a medical device having a structural unit represented by the formula (4) (described later) will be referred to as "the polymer for a medical device of a third invention". These three polymers will be collectively referred to as "the polymer for a medical device of the present invention", which is also simply referred to as "the polymer of the present invention".

The preferred embodiment of any one of the polymers for a medical device according to the first to third inventions serves also as the preferred embodiments of the remaining two of the polymers for a medical device of the first to third inventions.

<Polymer for a Medical Device of the First Invention>

The polymer for a medical device of the first invention is characterized by having a structural unit derived from a glycerol group-containing monomer and a structural unit derived from an unsaturated monomer having a structure in which an organic group having a structure site having 4 or more carbon atoms continuously bound is bound to an ethylenically unsaturated group; and satisfying a glass-transition temperature of 10° C. or less and/or a glass-transition temperature of −25° C. or less at a saturated water content.

The polymer for a medical device of the first invention is sufficient if it satisfies at least one of the requirements: the glass-transition temperature is 10° C. or less and the glass-transition temperature at a saturated water content is −25° C. or less, and may satisfy both requirements.

If the polymer for a medical device of the first invention satisfies a requirement of the glass-transition temperature being 10° C. or less, the glass-transition temperature is preferably 0° C. or less, more preferably −5° C. or less and further preferably −10° C. or less. Although the lower limit of the glass-transition temperature is not specified, the glass-transition temperature of polymer is usually −100° C. or more.

If the polymer for a medical device of the first invention satisfies a requirement of the glass-transition temperature at a saturated water content being −25° C. or less, the glass-transition temperature at a saturated water content is preferably −30° C. or less, more preferably −35° C. or less and further preferably −40° C. or less. Although the lower limit of the glass-transition temperature at a saturated water content is not particularly limited, glass-transition temperature of polymer at a saturated water content is usually −150° C. or more.

The glass-transition temperature of the polymer for a medical device of the present invention and the glass-transition temperature thereof at a saturated water content can be measured by the method described in Examples.

The polymer for a medical device of the first invention has a structural unit derived from a glycerol group-containing monomer and a structural unit derived from an unsaturated monomer having a structure in which an organic group having a structure site having 4 or more carbon atoms continuously bound is bound to an ethylenically unsaturated group. These structural units may be contained alone and in combination of two or more. The organic group having a structure site having 4 or more carbon atoms continuously bound may be bound to an ethylenically unsaturated group directly or via any structural unit (e.g., —O—, —C(=O)—, —C(=O)—O—, —N(=O)—O—). Note that, in the present invention, the structure derived from an unsaturated monomer is typically a structure formed by polymerizing an unsaturated monomer. Note that, not only a structure formed by actually polymerizing an unsaturated monomer but also a structure identical with the structure formed by actually polymerizing an unsaturated monomer corresponds to the structural unit derived from an unsaturated monomer. The structural unit derived from an unsaturated monomer typically refers to a structural unit obtained by substituting a carbon-carbon double bond (C=O) of an unsaturated monomer with a carbon-carbon single bond (—C—C—) and a structural unit having a ring formed by cyclopolymerization of a monomer having two or more of the unsaturated bonds.

The structure site refers to a site constituting a part of the structure of an organic group. The organic group having a structure site having 4 or more carbon atoms continuously bound may have the structure site having 4 or more carbon atoms continuously bound at an end of the organic group or at a portion other than the ends.

The polymer for a medical device of the first invention has at least two types of structural units, i.e., a structural unit derived from a glycerol group-containing monomer and a structural unit derived from an unsaturated monomer having a structure in which an organic group having a structure site having 4 or more carbon atoms continuously bound is bound to an ethylenically unsaturated group. These plurality of structural units may have any form, i.e., may be a random polymer, a graft polymer, a block polymer and an alternate polymer, and more preferably a random copolymer because antithrombogenicity significantly improves.

The structural unit derived from a glycerol group-containing monomer is not particularly limited as long as it is a structural unit derived from a monomer having a glycerol group and an ethylenically unsaturated bond (site); however, the structural unit is preferably represented by the following formula (1-1) and/or (1-2):

[Formula 1]

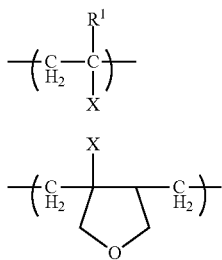

(1-1)

(1-2)

where $R^1$ represents a hydrogen atom, a methyl group or $-R^5-Y$, in which $R^5$ represents $-CH_2-$ or $-CH_2CH_2-$; X and Y represent a group represented by the following formula (2) or $-CO-O-R^6$, in which $R^6$ is an organic group having 1 to 24 carbon atoms; and at least one of X and Y is a group represented by the following formula (2).

[Formula 2]

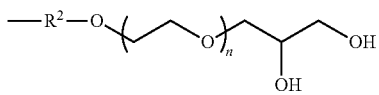

(2)

where $R^2$ represents $-CH_2-$, $-CO-$ or a direct bond; and n represents a number of 0 to 20.

In the above formula (1-1), the organic group represented by $R^6$ is preferably a hydrocarbon group and more preferably an alkyl group.

In the above formula (2), n is a number of preferably 0 to 15, more preferably 0 to 10 and further preferably 0 to 5.

Of these structural units, the structural unit derived from a glycerol group-containing monomer has a structural unit derived from glycerol (meth)acrylate or a derivative thereof. In other words, it is a preferred embodiment of the polymer for a medical device of the first invention that the polymer for a medical device of the first invention has a structural unit derived from glycerol (meth)acrylate or a derivative thereof.

The structural unit derived from an unsaturated monomer having a structure in which an organic group having a structure site having 4 or more carbon atoms continuously bound is bound to an ethylenically unsaturated group is preferably a structural unit derived from a (meth)acrylate to which an organic group having 4 or more carbon atoms continuously bound is bound, in other words, a preferable structural unit is represented by the following formula (3)

[Formula 3]

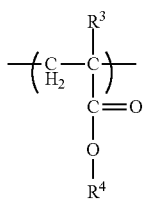

(3)

where $R^3$ represents a hydrogen atom or a methyl group; and $R^4$ represents an organic group having 4 or more carbon atoms continuously bound.

The organic group having 4 or more carbon atoms continuously bound represented by $R^4$ is preferably an organic group having 4 to 15 carbon atoms and more preferably 4 to 10 carbon atoms.

As the organic group having 4 or more carbon atoms continuously bound represented by $R^4$, any one of an alkyl group, an alkenyl group, an alkynyl group, an aryl group and an aralkyl group is mentioned. In addition, groups having a structure obtained by substituting a part of hydrogen atoms of these groups with a substituent such as a carboxyl group, a carboxyl salt, a hydroxy group, an epoxy group, an amino group and an alkoxy group.

Examples of the monomer forming a structural unit represented by the above formula (3) include (meth)acrylates such as n-butyl (meth)acrylate, s-butyl (meth)acrylate, t-butyl (meth)acrylate, n-amyl (meth)acrylate, s-amyl (meth)acrylate, t-amyl (meth)acrylate, n-hexyl (meth)acrylate, 2-ethylhexyl (meth)acrylate, isodecyl (meth)acrylate, tridecyl (meth)acrylate, cyclohexyl (meth)acrylate, cyclohexylmethyl (meth)acrylate, octyl (meth)acrylate, lauryl (meth)acrylate, stearyl (meth)acrylate, benzyl (meth)acrylate, phenyl (meth)acrylate, isobornyl (meth)acrylate, adamantyl (meth)acrylate, tricyclodecanyl (meth)acrylate, 2-hydroxybutyl (meth)acrylate, 3-hydroxybutyl (meth)acrylate, 4-hydroxybutyl (meth)acrylate, 2-ethoxyethyl (meth)acrylate, phenoxyethyl (meth)acrylate, tetrahydrofurfuryl (meth)acrylate, β-methylglycidyl (meth)acrylate, β-ethylglycidyl (meth)acrylate, (3,4-epoxycyclohexyl)methyl (meth)acrylate and N,N-dimethylaminoethyl (meth)acrylate.

Of the structural units derived from an unsaturated monomer having a structure in which an organic group having a structure site having 4 or more carbon atoms continuously bound is bound to an ethylenically unsaturated group, the structural units except those derived from (meth)acrylates include vinyl ethers such as butyl vinyl ether, 2-ethyl hexyl vinyl ether, dodecyl vinyl ether, stearyl vinyl ether, diethylene glycol vinyl ether and triethylene glycol vinyl ether; N-vinyls such as N-vinylpyrrolidone, N-vinyl morpholine, N-vinylcaprolactam and N-vinylcarbazole; and N-substituted maleimides such as N-phenylmaleimide, N-benzylmaleimide, N-naphthylmaleimide, N-cyclohexylmaleimide, N-butylmaleimide, N-isopropylmaleimide and N-ethylmaleimide.

A monomer component serving as a material for the polymer for a medical device of the first invention may contain another monomer except a glycerol group-containing monomer and an unsaturated monomer having a structure in which an organic group having a structure site having 4 or more carbon atoms continuously bound is bound to an ethylenically unsaturated group.

Examples of the "another monomer" include alkyl (meth)acrylates such as methyl (meth)acrylate, ethyl (meth)acrylate and propyl (meth)acrylate; vinyl esters such as vinyl acetate and vinyl propionate; vinyl chloride and vinylidene chloride; olefins such as ethylene, propylene, butene and isoprene; N-vinyl compounds such as N-vinylformamide and N-vinylacetamide; vinyl ethers such as methyl vinyl ether, ethyl vinyl ether and propyl vinyl ether; and methyl maleimide. These can be used alone or in combination of two or more.

In the polymer for a medical device of the first invention, the ratio of the structural unit derived from a glycerol group-containing monomer relative to all structural units (100 mass %) contained in the polymer is preferably 5 to 90 mass %. If such a ratio is satisfied, the polymer for a medical device of the first invention becomes more excellent in e.g., antithrombogenicity. The ratio of the structural unit derived from a glycerol group-containing monomer is more preferably 10 to 60 mass % and further preferably 20 to 50 mass %.

In the polymer for a medical device of the first invention, the ratio of the structural unit derived from an unsaturated monomer having a structure in which an organic group having a structure site having 4 or more carbon atoms continuously bound is bound to an ethylenically unsaturated group relative to all structural units (100 mass %) contained in the polymer is preferably 10 to 95 mass %, more preferably 10 to 60 mass % and further preferably 20 to 50 mass %.

Of them, the ratio of the structural unit represented by the above formula (3) relative to all structural units (100 mass %) contained in the polymer, is preferably 10 to 95 mass %, more preferably 10 to 60 mass % and further preferably 20 to 50 mass %.

If the polymer for a medical device of the first invention has a structural unit derived from the "another monomer" as mentioned above, the ratio thereof relative to all structural units (100 mass %) contained in the polymer is preferably 20 mass % or less, more preferably 10 mass % or less and further preferably 5 mass % or less.

<Polymer for a Medical Device of the Second Invention>

The polymer for a medical device of the second invention is characterized by having a glycerol group in a ratio of 1 mmol or more per 1 g of polymer and satisfying a glass-transition temperature of 10° C. or less and/or a glass-transition temperature of −25° C. or less at a saturated water content.

Also in the polymer for a medical device of the second invention, if the glass-transition temperature of 10° C. or less and/or the glass-transition temperature of −25° C. or less at a saturated water content are satisfied, the polymer becomes excellent in surface hydrophilicity and antithrombogenicity.

With respect to the glass-transition temperature of the polymer for a medical device of the second invention, the glass-transition temperature is 10° C. or less and/or the glass-transition temperature at a saturated water content is −25° C. or less. The preferable values of the glass-transition temperature and the glass-transition temperature at a saturated water content are the same as specified in the case where the glass-transition temperature of the polymer for a medical device of the first invention is 10° C. or less and the glass-transition temperature at a saturated water content is −25° C. or less.

The polymer for a medical device of the second invention has a glycerol group in a ratio of 1 mmol or more per 1 g of polymer. The amount of glycerol group per 1 g of polymer is preferably 1.5 mmol or more. If the ratio is satisfied, the polymer for a medical device of the second invention becomes more excellent in e.g., antithrombogenicity. The amount of glycerol group is more preferably 2 mmol or more. The amount of glycerol group per 1 g of polymer is preferably 6 mmol or less, more preferably 5 mmol or less and further preferably 4 mmol or less.

The polymer for a medical device of the second invention has a structural unit having a glycerol group. The structural unit having a glycerol group is preferably a structural unit derived from a glycerol group-containing monomer that the polymer for a medical device of the first invention has.

The polymer for a medical device of the second invention may have another structural unit except the structural unit having a glycerol group. Examples of the "another structural unit" include a structural unit derived from a (meth)acrylate represented by the above formula (3) (note that, the number of carbon atoms of $R^4$ in formula (3) may not be 4 or more) and a structural unit derived from the "another monomer" described above.

Examples of the (meth)acrylate represented by the above formula (3) (note that, the number of carbon atoms of $R^4$ in formula (3) may not be 4 or more) include, other than examples of a monomer forming a structure unit represented by the above formula (3), (meth)acrylates such as methyl (meth)acrylate, ethyl (meth)acrylate, n-propyl (meth)acrylate, i-propyl (meth)acrylate, 2-hydroxyethyl (meth)acrylate, 2-hydroxypropyl (meth)acrylate, 3-hydroxypropyl (meth)acrylate, 2-methoxyethyl (meth)acrylate, glycidyl (meth)acrylate, methyl α-hydroxymethylacrylate and ethyl α-hydroxymethylacrylate.

When the polymer for a medical device of the second invention has another structural unit except the structural unit having a glycerol group, the polymer preferably has a structural unit derived from butyl acrylate among the aforementioned (meth)acrylates.

In the case where the polymer for a medical device of the second invention has another structural unit except the structural unit having a glycerol group, the ratio thereof relative to all structural units (100 mass %) contained in the polymer is preferably 10 to 95 mass %, more preferably 20 to 90 mass % and further preferably 30 to 80 mass %.

<Polymer for a Medical Device of the Third Invention>

The polymer for a medical device of the third invention has a structural unit represented by the following formula (4):

[Formula 1]

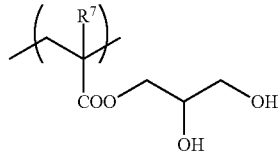

(4)

where $R^7$ represents a hydrogen atom or a methyl group.

The polymer having such a structural unit can be suitably used as a medical device material.

The polymer for a medical device of the third invention preferably has a molecular weight distribution of less than 5. The molecular weight distribution is defied by the ratio of a weight-average molecular weight relative to a number average molecular weight.

The polymer for a medical device of the third invention is preferably produced by using a monomer composition (described later) for a polymer for use in producing a medical device of the present invention or produced by polymerizing a monomer composition containing a monomer having a glycidyl and/or a ketalized glycerol group, followed by hydrolyzing the glycidyl and/or ketalized glycerol group. In the case where a polymer is produced by using a monomer composition for a polymer for use in producing a medical device containing crosslinkable impurities such as a compound having two or more (meth)acryloyl groups in a molecule, as a starting composition, a cross-linking reaction takes place due to the impurities, with the result that the polymer has a large molecular weight distribution. If the molecular weight distribution becomes large, biocompatibility of the polymer tends to reduce. Although the reason is unknown, if the molecular weight distribution increases, a crosslinked minor component called microgel (it is very difficult to quantitatively detect it) conceivably generates. Since the microgel contains highly densely crosslinked molecules, the mobility of molecular chains is low. Because of this, it is considered that the content of intermediate water is low and the amount of nonfreezing water is high. As a result, a biological defense mechanism is presumably activated. In addition, if a microgel is present, when the polymer is applied to a substrate to form a coating, the surface thereof loses smoothness and a bumpy surface is resulted, inviting retention of proteins. Further, nonfreezing water on the surface of the microgel easily comes into contact with the proteins. Presumably, biocompatibility tends to reduce. The molecular weight distribution of the polymer to be used for a medical device is preferably less than 5, more preferably less than 4 and further preferably less than 3.

The molecular weight distribution of the polymer can be measured by gel permeation chromatography (GPC) in the conditions described in Examples.

In the conditions where a microgel can be formed, insoluble matter unfavorable in view of biocompatibility is sometimes produced. In the polymer as mentioned above, the content of an insoluble matter is preferably 10 mass % or less. The material to be used in a medical device is preferably less contaminated with insoluble matter. The content of the insoluble matter relative to the weight of the polymer is preferably 10 mass % or less, more preferably 5 mass % or less, further preferably 1 mass % or less and particularly preferably 0.1 mass % or less.

Note that the insoluble matter used herein refers to a polymer component that becomes insoluble in a solvent due to cross-linking reaction. The presence of insoluble matter can be visually observed, since the insoluble matter remains on the wall surface when a polymer solution having a concentration 10% or less is placed in a container such as a glass container and allowed to flow. The quantitative determination is more specifically as follows. A copolymer solution prepared so as to have a concentration 10% or less was passed through a filter having 0.45 μm-openings and the insoluble matter remaining on the filter was washed with a solvent. The filter is dried (for example, dried at 80° C. for one hour) to remove the solvent and then the weight of the filter is measured to obtain an increased weight (before and) after the filtration. The content of the insoluble matter is obtained based on the following expression. In the case where the content of insoluble matter is excessively large, a filter is clogged and filtration cannot be made.

Content of insoluble matter (%)=[increased weight (g)/polymer solid matter (g)]×100

Note that, the solvent to be used for determining the content of insoluble matter is selected from the solvents that can fully dissolve a polymer not gelatinized. When the content of the insoluble matter is determined by a method of filtration through the filter, the concentration of the insoluble matter is appropriately controlled so as not to leave insoluble matter unsolved and increase the viscosity of the solution excessively.

The polymer having a structural unit represented by the above formula (4) preferably contains a structural unit represented by the formula (4) in a content of 5 to 90 mol % relative to all structural units (100 mol %). The polymer to be used in a medical device is required to have high affinity for a biogenic substance and a body tissue and excellent adhesiveness to the material to be used as a base material for a medical device; at the same time, the polymer is required not to be dissolved with a biogenic substance and a body tissue. To satisfy both requirements, a structural unit represented by the formula (4) is preferably contained in the aforementioned ratio.

The content of a structural unit represented by the formula (4) is more preferably 10 to 60 mol %, further preferably 15 to 50 mol % and particularly preferably 20 to 40 mol %.

If a polymer having a structural unit represented by the above formula (4) is a copolymer having another structural unit except the structural unit represented by the above formula (4), the copolymer may have any form, i.e., may be any one of a random polymer, a graft polymer, a block polymer and an alternate polymer. In order to form a uniform surface and reproducibly exhibit stable biocompatibility, the copolymer is preferably a random polymer.

A polymer having a structural unit represented by the above formula (4) preferably has a structural unit derived from a monomer whose homopolymer has a glass transition temperature of 50° C. or less. If a polymer has such a structural unit, the polymer becomes sufficiently flexible in the temperature range where a medical device is used and becomes more suitable as a polymer for use in a medical device.

A monomer forming a structural unit as mentioned above is preferably a monomer whose homopolymer has a glass transition temperature of 50° C. or less, more preferably a monomer whose homopolymer has a glass transition temperature of 40° C. or less, further preferably a monomer whose homopolymer has a glass transition temperature of 30° C. or less and particularly preferably a monomer whose homopolymer has a glass transition temperature of 20° C. or less. As the monomer forming a structural unit as mentioned above, a monomer whose homopolymer has a glass transition temperature of −80° C. or more is usually preferred.

The glass transition temperature of the homopolymer can be measured by a DSC (differential scanning calorimeter).

In the case where a polymer having a structural unit represented by the above formula (4) has a structural unit derived from a monomer whose homopolymer has a glass transition temperature of 50° C. or less, the content of the structural unit relative to all structural units (100 mol %) of the polymer is preferably 90 to 10 mol %, more preferably 85 to 20 mol %, further preferably 80 to 30 mol % and particularly preferably 70 to 40 mol %.

Examples of the monomer whose homopolymer has a glass transition temperature of 50° C. or less include 2-ethylhexyl (meth)acrylate, butyl (meth)acrylate, ethyl acrylate, methyl acrylate, hydroxyethyl acrylate, glycidyl (meth)acrylate and vinyl acetate. These can be used alone or in combination of two or more.

The polymer having a structural unit represented by the above formula (4) may have another structural unit except the structural unit represented by the formula (4) and the structural unit derived from a monomer whose homopolymer has a glass transition temperature of 50° C. or less. In the case where another monomer unit is contained, the content of the structural unit relative to all structural units (100 mol %) of the polymer is preferably 50 mol % or less, more preferably 30 mol % or less, further preferably 20 mol % or less and particularly preferably 10 mol % or less.

Examples of the monomer constituting the structural unit except the structural unit represented by the above formula (4) and the structural unit derived from a monomer whose homopolymer has a glass transition temperature of 50° C. or less include styrene, methyl methacrylate, ethyl methacrylate, hydroxyethyl methacrylate, acrylic acid, methacrylic acid, isopropenyl oxazoline and phenylmaleimide. These can be used alone or in combination of two or more.

In the polymer having a structural unit represented by the above formula (4), the content of a structural unit derived from a compound having two or more (meth)acryloyl groups in a single molecule relative to all structural units (100 mol %) constituting the polymer, is preferably 0.15 mol % or less. The polymer having a low content of a structural unit derived from such a crosslinkable monomer is not easily gelatinized and becomes more suitable as a a medical device material. The content of a structural unit derived from a compound having two or more (meth)acryloyl groups in a single molecule relative to all structural units (100 mol %) constituting the polymer, is more preferably 0.1 mol % or less, further preferably 0.05 mol % or less, and particularly preferably 0.01 mol % or less.

Such a polymer can be obtained by polymerization of a material having a low content of a compound having two or more (meth)acryloyl groups in a single molecule.

Note that, the structural unit derived from a compound having two or more (meth)acryloyl groups in a single molecule refers to a structural unit formed by subjecting a compound having two or more (meth)acryloyl groups in a single molecule to a polymerization reaction, and more specifically, refers to a structural unit obtained by replacing at least one carbon-carbon double bond contained in a compound having two or more (meth)acryloyl groups in a single molecule, with a carbon-carbon single bond.

<Polymer for a Medical Device of the Present Invention>

Now, common matters in the polymers for a medical device of first to third inventions will be described.

It is preferable that the polymer for a medical device of the present invention has a weight-average molecular weight of 1,000 to 10,000,000. It is preferable because the polymer having the weight-average molecular weight falls within the range becomes the material having excellent durability and mechanical strength. The weight-average molecular weight is more preferably 5,000 to 2,000,000, further preferably 5,000 to 1,000,000, particularly preferably 10,000 to 500,000 and most preferably 50,000 to 500,000.

In the polymer for a medical device of the present invention, the ratio of a component having a molecular weight of 5000 or less relative to the whole polymer is more preferably 5.0% or less. If the ratio of a component having a molecular weight of 5000 or less relative to the whole polymer is 5.0% or less, elution of low-molecular-weight components into the blood can be suppressed even if it is used for a long-term and affinity of the polymer for a body tissue becomes more satisfactory. The ratio of the component having a molecular weight of 5000 or less is further preferably 1.0% or less of the whole polymer and particularly preferably 0.5% or less of the whole polymer.

The weight-average molecular weight of the polymer and the ratio of the component having a molecular weight of 5000 or less can be measured by gel permeation chromatography (GPC) in the measurement conditions described in Examples.

<Method for Producing a Glycerol Group-Containing Monomer>

Of the structural units represented by the above formula (1-1), a structural unit where $R^1$ represents a hydrogen atom or a methyl group is a glycerol group-containing monomer represented by the following formula (5):

[Formula 4]

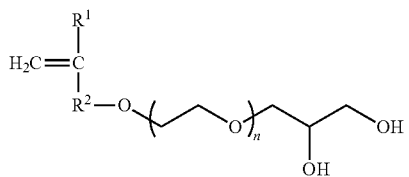

(5)

where $R^1$ represents a hydrogen atom or a methyl group; $R^2$ represents —$CH_2$—, —CO— or a direct bond; and n represents a number of 0 to 20.

As a method for producing the glycerol group-containing monomer, which is not particularly limited, it is preferable to employ a method of reacting a vinyl compound represented by the following formula (6):

[Formula 5]

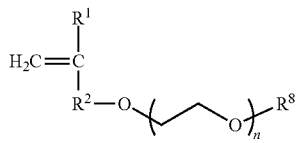

(6)

where $R^1$, $R^2$ and n are the same as defined in formula (5); and $R^8$ represents a hydrogen atom, an alkali metal atom, an ammonium group or a hydrocarbon group having 1 to 30 carbon atoms, and a ketalized glycerol compound represented by the following formula (7):

[Formula 6]

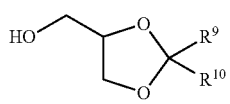

(7)

where $R^9$ and $R^{10}$, which may be the same or different, each represents a hydrogen atom or a hydrocarbon group having 1 to 30 carbon atoms, or epichlorohydrin and reacting water with the resultant product.

The compound represented by the above formula (6) can be produced by, for example, reacting a vinyl compound represented by the following formula (8):

[Formula 7]

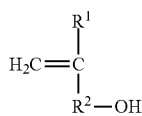

(8)

where $R^1$ and $R^2$ are the same as defined in formula (5), and ethylene oxide.

Of the structural units represented by the above formula (1-1), a structural unit where $R^1$ is —$R^5$—Y, can be produced by appropriately selecting a vinyl compound with reference to the above reaction.

A structural unit represented by the above formula (1-2) can be formed by using e.g., a compound represented by the following formula (9):

[Formula 8]

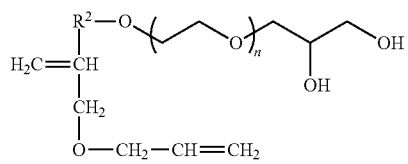

where $R^2$ represents —$CH_2$—, —CO— or a direct bond; and n represents a number of 0 to 20. The compound represented by the formula (9) is a derivative of glycerol (meth)acrylate. The compound represented by the above formula (9) can be produced in the same manner as in the method for producing a glycerol group-containing monomer represented by the above formula (5) except that a compound represented by the following formula (10):

[Formula 9]

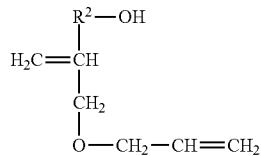

where $R^2$ is the same as defined in formula (9) is used in place of the vinyl compound represented by the above formula (8).

Examples of the alkali metal atom represented by $R^8$ in the above formula (6) include a sodium atom and a potassium atom.

The hydrocarbon group having 1 to 30 carbon atoms represented by each of $R^8$ to $R^{10}$ in the above formulas (6) and (7) is not particularly limited; however, in view of the reactivity, the hydrocarbon group is preferably a hydrocarbon group having 1 to 20 carbon atoms, more preferably a hydrocarbon group having 1 to 10 carbon atoms and further preferably a hydrocarbon group having 1 to 5 carbon atoms.

As the hydrocarbon group, any one of an alkyl group, an alkenyl group, an alkynyl group, an aryl group and an aralkyl group may be used.

Note that, $R^8$ to $R^{10}$ may be the same or different.

Examples of the compound represented by the above formula (10) include allyloxymethylacrylic acid.

In a step of reacting a vinyl compound represented by the above formula (6) and a ketalized glycerol compound represented by the above formula (7) or epichlorohydrin (hereinafter also referred to as the first step) the ketalized glycerol compound or epichlorohydrin is preferably used in a ratio of 0.05 to 20 moles relative to the vinyl compound (1 mole), more preferably 0.1 to 10 moles and further preferably 0.2 to 5 moles.

Note that, in the first step, either one or both of the ketalized glycerol compound and epichlorohydrin may be used. If both compounds are used, the total use amount preferably falls within the aforementioned ratio range.

The reaction of the first step may be carried out by use of a catalyst. Examples of the catalyst include titanium compounds such as titanium tetramethoxide, titanium tetraethoxide, titanium tetraisopropoxide, titanium tetrabutoxide, titanium tetrakis(2-ethylhexyloxide) and titanium tetrastearyloxide; tin compounds such as di-n-butyltin oxide, di-n-octyltin oxide, di-n-butyltin dimethoxide, di-n-butyltin diacrylate, di-n-butyltin dimethacrylate and di-n-butyltin dilaurate; and an oxide, chloride and carbonate of a metal atom belonging to the first family or second family of the periodic table such as lithium, potassium, magnesium and calcium. These can be used alone or in combination of two or more.

If the catalyst is used, the use amount thereof may be appropriately set; however, the use amount is preferably 0.1 to 10 mass % relative to the glycerol compound represented by the above formula (7) or epichlorohydrin (100 mass %) and more preferably 0.5 to 5 mass %.

When a ketalized glycerol compound and epichlorohydrin are both used in the first step, the ratio of a catalyst relative to the total use amount of both compounds preferably falls within the aforementioned range.

The reaction of the first step may be carried out in the presence of a solvent. Examples of the solvent include toluene, xylene, benzene, hexane, cyclohexane, methyl ethyl ketone, methyl isobutyl ketone and acetone. These can be used alone or in combination of two or more.

The reaction of the first step is carried out at a temperature of preferably 20 to 150° C. and more preferably 50 to 100° C.

The reaction of the first step may be carried out under ordinary pressure, increased pressure or reduced pressure.

The reaction of the first step is a transesterification reaction. Because of this, in order to improve the yield of a reaction product, the reaction is preferably carried out while removing the reaction product and/or a by-produced alcohol.

A method of removing the reaction product and/or by-produced alcohol is not particularly limited; e.g., distillation can be used.

A step of obtaining a glycerol group-containing monomer represented by the formula (5) by reacting water with a reaction product of the first step (hereinafter also referred to as the second step) is preferably carried out in the presence of a catalyst.

Examples of the catalyst include acid catalysts such as an organic acid, an inorganic acid, a cation exchange resin and an inorganic solid acid. These can be used alone or in combination of two or more.

Examples of the organic acid include formic acid, acetic acid, p-toluene sulfonic acid and methane sulfonic acid. Examples of the inorganic acid include hydrochloric acid, sulfuric acid, nitric acid and phosphoric acid.

As the cation-exchange resin, a strong acidic ion-exchange resin is preferable. Examples thereof include Amberlyst 15J wet, Amberlyst 15W (IR-200CH) (manufactured by ORGANO CORPORATION); RCP-160M, RCP-150H, RCP-170H and PK-216 (manufactured by Mitsubishi Chemical Corporation); and DOWEX 50W (manufactured by Dow Chemical).

As the inorganic solid acid, zeolite; a solid phosphoric acid; an inorganic solid acid obtained by treating the surface of a carrier formed of at least one inorganic substance selected from the group consisting of clay, silica, alumina and titanium oxide, with a mineral acid while heating (more specifically, e.g., activated earth) is mentioned. Of these, zeolite and an inorganic solid acid obtained by treating the surface of a carrier formed of at least one inorganic substance selected from the group consisting of clay, silica, alumina and titanium oxide, with a mineral acid while heating is preferable and zeolite is more preferable. Particularly, zeolite is preferably used as an inorganic solid acid catalyst since it can be easily regenerated by heating while supplying an inert gas such as nitrogen.

The use amount of the catalyst may be appropriately set. The use amount is preferably 0.001 to 20 mass % relative to the reaction product (100 mass %) obtained in the first step and more preferably 0.1 to 10 mass %.

The use amount of water in the reaction of the second step is preferably 1 mole or more relative to the reaction product (one mole) obtained in the first step and more preferably 3 moles or more. Since water serves as a solvent in the reaction of the second step, the upper limit of the use amount of water is not specified; however, a reaction can be carried out in the presence of water in an amount of, for example, 50 moles or less relative to the reaction product (one mole) obtained in the first step.

The reaction in the second step is carried out at a temperature of preferably −10 to 150° C. and more preferably 20 to 100° C.

The reaction in the second step may be carried out under ordinary pressure, increased pressure or reduced pressure.

In the reactions of the first step and the second step, in order to suppress polymerization of a vinyl compound, it is preferable to use a polymerization inhibitor and/or carry out the reaction while the reaction solution is bubbled with an oxygen-containing gas.

Examples of the polymerization inhibitor that can be used include a polymerization inhibitor based on a quinone such as hydroquinone, methoxy hydroquinone, benzoquinone and p-tert-butylcatechol; a polymerization inhibitor based on an alkylphenol such as 2,6-di-tert-butylphenol, 2,4-di-tert-butylphenol, 2-tert-butyl-4,6-dimethylphenol, 2,6-di-tert-butyl-4-methylphenol and 2, 4,6-tri-tert-butyl phenol; a polymerization inhibitor based on an amine such as an alkylated diphenylamine, N,N'-diphenyl-p-phenylenediamine, phenothiazine, 4-hydroxy-2,2,6,6-tetramethylpiperidine, 4-benzoyloxy-2,2,6,6-tetramethylpiperidine, 1,4-dihydroxy-2,2,6,6-tetramethylpiperidine and 1-hydroxy-4-benzoyloxy-2,2,6,6-tetramethylpiperidine; and a polymerization inhibitor based on N-oxyl such as 2,2,6,6-tetramethylpiperidine-N-oxyl, 4-hydroxy-2,2,6,6-tetramethylpiperidine-N-oxyl and 4-benzoyloxy-2,2,6,6-tetramethylpiperidine-N-oxyl.

Among these, hydroquinone, methoxyhydroquinone, benzoquinone, p-tert-butylcatechol, phenothiazine, 2,2,6,6-tetramethylpiperidine-N-oxyl, 4-hydroxy-2,2,6,6-tetramethylpiperidine-N-oxyl and 4-benzoyloxy-2,2,6,6-tetramethylpiperidine-N-oxyl can be used alone or in combination of two or more.

The use amount of the polymerization inhibitor relative to the vinyl compound (100 mass %) is preferably 0.0005 to 5 mass % and more preferably 0.005 to 0.5 mass %.

In the case where the reaction is carried out while the reaction solution is bubbled with an oxygen-containing gas, the concentration of oxygen in the gas for use in bubbling is preferably 1 vol % or more.

The reaction between a vinyl compound represented by the above formula (6) and a ketalized glycerol compound represented by the above formula (7) or epichlorohydrin can be carried out at a temperature appropriately set within the range of −10 to 150° C. under ordinary pressure, increased pressure or reduced pressure.

Of the aforementioned reactions, in the step where water is reacted with the reaction product between a vinyl compound represented by the above formula (6) and a ketalized glycerol compound represented by the above formula (7) or epichlorohydrin, one or two or more acid catalysts such as an acid (e.g., hydrochloric acid and sulfuric acid), an inorganic solid acid and a cation-exchange resin are preferably used.

In the above reaction, in order to suppress polymerization of a vinyl compound, it is preferable to use a polymerization inhibitor and/or carry out the reaction while the reaction solution is bubbled with an oxygen-containing gas.

<Method of Producing a Polymer for a Medical Device>

The polymer for a medical device of the present invention can be produced by appropriately selecting a monomer so as to obtain the aforementioned characteristics and subjecting the monomer to a polymerization reaction.

A preferable use amount of such a monomer in a material for a polymer is the same as the preferable ratio of the structural units derived from these monomer in all monomer units of the polymer for a medical device of the present invention.

In the method of producing a polymer for a medical device, the polymerization reaction is preferably carried out in the presence of a polymerization initiator. Examples of a preferable polymerization initiator include hydrogen peroxide; a persulfate such as sodium persulfate, potassium persulfate and ammonium persulfate; an azo compound such as dimethyl 2,2'-azobis(2-methylpropionate) and 2,2'-azobis (isobutyronitrile); and an organic peroxide such as benzoyl peroxide, peracetic acid and di-t-butyl peroxide. These polymerization initiators may be used alone or as a mixture of two or more.

The use amount of a polymerization initiator relative to the use amount (1 mole) of monomer to be used in a polymerization reaction is preferably 0.01 g or more and 10 g or less and more preferably 0.1 g or more and 5 g or less.

The polymerization reaction may be carried out in the absence of a solvent; however, a solvent is preferably used.

Examples of the solvent include acetonitrile, tetrahydrofuran, dioxane, acetone, methyl ethyl ketone, methyl isobutyl ketone, methanol, ethanol and isopropyl alcohol. These solvents may be used singly or as a mixture of two or more.

The use amount of solvent relative to the monomer (100 mass %) in a polymerization reaction is preferably 40 to 250 mass %.

The polymerization reaction is preferably carried out usually at 0° C. or more, preferably at 150° C. or less, more preferably 40° C. or more, further preferably 60° C. or more and particularly preferably 80° C. or more; and more preferably 120° C. or less and further preferably 110° C. or less. It is not necessary to always keep the temperature of a polymerization reaction at an almost constant value, and the polymerization temperature may be changed once or twice or more (heating or cooling). The polymerization reaction may be carried out under ordinary pressure, increased pressure or reduced pressure.

In the above polymerization reaction, a material monomer for a polymer for a medical device and e.g., a polymerization initiator may be simultaneously and sequentially added to a reactor.

The method for producing the polymer for a medical device of the present invention may contain a step other than the polymerization reaction step. Examples thereof include an aging step, a neutralization step, an inactivation step of a polymerization initiator and a chain transfer agent, a dilution step, a drying step, a concentration step and a purification step.

Now, the monomer composition for a polymer for use in producing a medical device of the present invention will be described below. A preferable embodiment of a polymer for a medical device obtained from the monomer composition for a polymer for use in producing a medical device of the present invention that will be described below is also the preferable embodiment of the polymer for a medical device of the present invention.

It is one of the suitable embodiment of the present invention that the polymer for a medical device of the present invention is obtained from the monomer composition for a polymer for use in producing a medical device of the present invention.

<Monomer Composition for a Polymer for Use in Producing a Medical Device>

The present invention also relates to a monomer composition for use in producing a polymer for a medical device, wherein the monomer composition comprises a glycerol group-containing monomer and the content of a compound having two or more (meth)acryloyl groups in a single molecule is 0.3 mass % or less relative to the glycerol group-containing monomer (100 mass %).

Since a glycerol group-containing monomer such as glycerol mono(meth)acrylate is easily gelatinized, it is difficult to produce a polymer. Because of this, the copolymers specifically described in Patent Literatures 1, 2, 4 and 5 all contain a structural unit derived from glycerol mono(meth)acrylate in a small ratio. The copolymers described in Patent Literatures 3 and 6 contain a structural unit derived from glycerol mono(meth)acrylate in a larger ratio than those described in other Patent Literatures. However, Patent Literature 3 discloses only the copolymer with a specific compound, i.e., 2-(methacryloyloxy)ethyl-2'-(trimethylammonio)ethyl phosphate (MPC). Also, Patent Literature 6 discloses only the production of a block copolymer that has the structural unit derived from styrene and the structural unit derived from glycerol monomethacrylate. Since a glycerol group-containing monomer such as glycerol mono(meth)acrylate is a compound having excellent biocompatibility, it is preferable that a copolymer is successfully and easily produced by mixing the glycerol group-containing monomer with many compounds in various ratios, in order to develop an excellent medical device material.

In connection with this, the present inventors found that by suppressing the content of a compound having two or more (meth)acryloyl groups in a single molecule within a predetermined ratio relative to a glycerol group-containing monomer, the glycerol group-containing monomer exhibits good polymerizability; and that even if a compound except a specific compound such as MPC is used, a polymer containing a structural unit derived from a glycerol group-containing monomer in a high ratio can be produced without through an intricate step of protecting and deprotecting a functional group.

The monomer composition for a polymer for use in producing a medical device of the present invention contains a glycerol group-containing monomer and crosslinkable monomers as impurities within a specific ratio or less. Due to this, the monomer composition for a polymer for use in producing a medical device of the present invention has good polymerizability and can be used as a starting material for a polymer excellent in biocompatibility. In addition, a polymer for a medical device having a structural unit corresponding to a polymer obtained by polymerizing an ethylenically unsaturated bond (site) of a glycerol group-containing monomer is excellent in biocompatibility and moldability (more specifically, excellent in coating property when the polymer is used as a component of a coating agent). Because of this, the polymer can be suitably used as a material for a portion of a medical device to be in contact with a body tissue and a biogenic substance, with the result that high-quality medical devices and others can be manufactured.

In the monomer composition for a polymer for use in producing a medical device, the content of a compound having two or more (meth)acryloyl groups in a single molecule relative to the glycerol group-containing monomer (100 mass %) is preferably 0.2 mass % or less and further preferably 0.1 mass % or less.

The content of a compound having two or more (meth)acryloyl groups in a single molecule relative to the glycerol group-containing monomer (100 mass %) in a monomer composition for a polymer for use in producing a medical device can be calculated based on the area ratio of the peak derived from a glycerol group-containing monomer and the peak derived from a compound having two or more (meth)acryloyl groups in a single molecule obtained by subjecting the monomer composition to gas chromatographic analysis.

In the monomer composition for a polymer for use in producing a medical device of the present invention, the content of a halogen relative to the glycerol group-containing monomer (100 mass %) is preferably 0.1 mass % or less. Since halogen has a possibility of forming a harmful organic halogen compound, the monomer composition for a polymer for use in producing a medical device of the present invention containing halogen within the ratio, is more suitable as a material for a polymer for a medical device. The content of a halogen relative to the glycerol group-containing monomer (100 mass %) is more preferably 0.01 mass % or less and particularly preferably 0.001 mass % or less.

Examples of the halogen include fluorine, chlorine and bromine.

The content of a halogen in a monomer composition for a polymer for use in producing a medical device can be measured by ion chromatography in accordance with the method described in Examples.

The glycerol group-containing monomer contained in the monomer composition for a polymer for use in producing a medical device of the present invention is not particularly limited as long as it has a glycerol group and an ethylenically unsaturated bond site; however, glycerin mono(meth)acrylate is preferable. The glycerin mono(meth)acrylate represents glycerin monoacrylate and/or glycerin monomethacrylate; however, glycerin monoacrylate is preferably contained in the monomer composition for a polymer for use in producing a medical device of the present invention.

Usually, when a polymer compound is hydrated, non-freezing water, which has a high interaction with the polymer compound and is not frozen, and free water, which has a poor interaction with the polymer compound, are present on the surface of the polymer compound. It has been found that some of polymer compounds have intermediate water, which has a medium-level interaction with the polymer compound. A biogenic substance and a body tissue form a hydration shell in the blood and the body fluid and are thus stable therein. However, if the hydration shell comes into contact with the nonfreezing water on the surface of a polymer compound, the hydration shell is destabilized or destroyed, with the result that a biogenic substance and a body tissue are adsorbed onto the surface of a polymer material and conceivably the biological defense mechanism is activated. In this case, if the intermediate water is stably present on an nonfreezing water layer on the polymer-material surface, even if the polymer comes into contact with a biogenic substance and a body tissue, proteins and a hydration structure of a cell surface are less likely to be destroyed. Such a polymer compound has been elucidated to have high biocompatibility. The present inventors have found that a structural unit represented by the above formula (4) is an extremely useful structure for holding intermediate water. More specifically, since a structural unit represented by the above formula (4) is extremely advantageous for holding intermediate water, a polymer having the structural unit represented by the above formula (4) holds intermediate water in a wide variety of compositions and thus a product excellent in biocompatibility is presumably obtained. The present inventors further found that a polymer produced from glycerin monoacrylate as a staring material holds a larger amount of intermediate water and a lower amount of nonfreezing water, than a polymer produced from glycerin monomethacrylate as a staring material. Because of this, a polymer obtained from the monomer composition for a polymer for use in producing a medical device of the present invention containing glycerin monoacrylate is more suitable as a medical device material.

In the case where the monomer composition for a polymer for use in producing a medical device of the present invention contains glycerin monoacrylate, the ratio of the glycerin monoacrylate relative to the whole glycerin mono(meth)acrylate contained in the monomer composition is preferably 50 mass % or more, more preferably 80 mass % or more, further preferably 90 mass % or more and most preferably 100 mass %, which is the case where the whole glycerin mono(meth)acrylate contained in the monomer composition is glycerin monoacrylate.

The monomer composition for a polymer for use in producing a medical device of the present invention can be preferably used as a starting material for, for example, the polymer for a medical device of the first invention, the polymer for a medical device of the second invention and the polymer for a medical device of the third invention.

According to the monomer composition for a polymer for use in producing a medical device of the present invention, it is possible to provide a glycerin mono(meth)acrylate having good polymerizability and suitably used as a starting material for the polymer to be used as a medical device material.

Glycerin mono(meth)acrylate is a compound having excellent biocompatibility. If the monomer composition for a polymer for use in producing a medical device of the present invention is used, it can be mixed with various materials in various ratios to produce a copolymer while suppressing gelatinization.

A method for producing the monomer composition for a polymer for use in producing a medical device of the present invention is not particularly limited; however, a method of reacting a vinyl compound and a ketalized glycerol compound and thereafter reacting water with the resultant product as described in the method for producing a glycerol group-containing monomer is preferable. If (meth)acrylic acid or a salt or an ester thereof is used as the vinyl compound, a dimerization reaction of the vinyl compound sometimes proceeds and a compound having two or more (meth)acryloyl groups in a single molecule is generated. However, in the above method, even if (meth)acrylic acid or a salt or an ester thereof is used as the vinyl compound, a transesterification reaction between the vinyl compound and the ketalized glycerol compound occurs to protect a car- boxyl group moiety. Since dimerization of the vinyl compound is suppressed from proceeding in this manner, glycerin mono(meth)acrylate can be produced while suppressing production of a compound having two or more (meth)acryloyl groups in a single molecule, and a monomer composition having a compound having two or more (meth)acryloyl groups in a single molecule in a content of 0.3 mass % or less relative to the glycerin mono(meth)acrylate (100 mass %) and suitable for a material for a polymer for a medical device can be produced.

Such a method for producing a monomer composition for a polymer for use in producing a medical device corresponds to the method for producing a glycerol group-containing monomer including a first step of reacting a vinyl compound represented by the above formula (6) where $R^2$ is —CO— and n is 0 and a glycerol compound represented by the above formula (7); and a second step of reacting water with the reaction product of the first step to obtain a glycerin mono(meth)acrylate represented by the above formula (5) where $R^2$ is —CO— and n is 0. Such method for producing a monomer composition for a polymer for use in producing a medical device including a step of reacting a vinyl compound and a ketalized glycerol compound and a step of reacting water with the reaction product of the reaction step to obtain a glycerin mono(meth)acrylate is also one of the present invention.

The method for producing the monomer composition for a polymer for use in producing a medical device of the present invention may include another step as long as the above first step and the second step are included. Examples of the "another step" include a concentration step and a purification step. For example, if necessary, a purification step of removing e.g., a compound having two or more (meth)acryloyl groups in a single molecule, may be provided.

The present invention also relates to, a method of producing a polymer for a medical device including a step of subjecting a monomer composition for a polymer for use in producing a medical device, which is obtained by the method for producing a monomer composition for a polymer for use in producing a medical device, to a polymerization reaction. As mentioned above, since the monomer composition for a polymer for use in producing a medical device obtained by the method for producing the monomer composition for a polymer for use in producing a medical device of the present invention has good polymerizability due to a small content of a compound having two or more (meth)acryloyl groups in a single molecule, copolymers with various monomers can be produced. When a polymer is produced by using the monomer composition for a polymer for use in producing a medical device which is obtained by the method for producing the monomer composition for a polymer for use in producing a medical device of the present invention, the resultant polymer has a low content of cross-linkable impurities and a narrower molecular weight distribution than the polymer using a glycerin mono(meth)acrylate produced by another production method.

A method for producing a polymer by using a composition containing a glycerol group-containing monomer and an unsaturated monomer having a structure in which an organic group having a structure site having 4 or more carbon atoms continuously bound is bound to an ethylenically unsaturated group, as the monomer composition for a polymer for use in producing a medical device, can be used as a method for producing the polymer for a medical device of the first invention. This case can be also said that a polymer is produced by using a monomer component, which contains a glycerol group-containing monomer, in which the content of a compound having two or more (meth)acryloyl groups in a single molecule relative to the glycerol group-containing monomer (100 mass %) is 0.3 mass % or less, and an unsaturated monomer having a structure in which an organic group having a structure site having 4 or more carbon atoms continuously bound is bound to an ethylenically unsaturated group.

Such a method for producing a polymer for a medical device, more specifically, a method of producing a polymer for a medical device including a step of subjecting a monomer component, which contains a glycerol group-containing monomer and an unsaturated monomer having a structure in which an organic group having a structure site having 4 or more carbon atoms continuously bound is bound to an ethylenically unsaturated group, to polymerization, wherein the content of a compound having two or more (meth)acryloyl groups in a single molecule in the glycerol group-containing monomer relative to the glycerol group-containing monomer (100 mass %) is 0.3 mass % or less, is also one of the present invention.

In this case, it is preferable that the mass ratio of the glycerol group-containing monomer and the unsaturated monomer having a structure in which an organic group having a structure site having 4 or more carbon atoms continuously bound is bound to an ethylenically unsaturated group in the monomer composition is the same as the mass ratio of structural units derived from these monomers relative to all structural units contained in the polymer for a medical device of the first invention.

In the method for producing a polymer for a medical device, a polymerization reaction can be carried out by using a monomer composition for a polymer for use in producing a medical device, and if necessary, another monomer.

As the "another monomer", a monomer whose, homopolymer has a glass transition temperature of 50° C. or less, as mentioned above, and a monomer forming a structural unit other than a structural unit derived from a glycerol group-containing monomer such as a structural unit represented by the above formula (4) and a structural unit derived a monomer whose homopolymer has a glass transition temperature of 50° C. or less, can be used.

The preferable use amount of these monomers in the material for polymer is the same as the preferable ratio of the structural units derived from these monomers in the all monomer units of the polymer having the structural unit represented by the above formula (4).

A preferable polymerization initiator, solvent, conditions such as a reaction temperature and pressure and steps that may be included other than the polymerization reaction step in the method for producing a polymer for a medical device are the same as specified in the section <Method of producing a polymer for a medical device>. Note that, when a monomer other than the monomer composition for a polymer for use in producing a medical device is used, a step of polymerizing the monomer in the presence of a monomer composition for a polymer for use in producing a medical device is preferably included.

<Medical Device Material, Antithrombogenic Coating Agent and Medical Device>

The polymer for a medical device of the present invention has excellent biocompatibility as described above and can be suitably used as a material for a medical device or a part (component) thereof. Such a medical device material containing the polymer for a medical device of the present invention is one aspect of the present invention and a method of using the polymer for a medical device of the present invention as a medical device material is also one aspect of the present invention. As the method of using the polymer for a medical device of the present invention, as a medical device material, e.g., a method of coating the surface of a medical device or a part thereof with the medical device material, and a method of molding the polymer for a medical device of the present invention into the shape of a medical device or a part thereof, are mentioned as described later.

Since the medical device material of the present invention has a high affinity for a biogenic substance and a body tissue, the material can be suitably used as an antithrombogenic material which is not likely to form thrombus even if it is in contact with blood, and can be suitably used as a material constituting portions of various medical devices or parts thereof to be in contact with a biogenic substance or a body tissue. Further, the medical device material of the present invention can be suitably used also as a cell culture medium.

The medical device or a part thereof obtained by using the medical device material of the present invention can be produced by a method of treating the surface of at least a part of the portion of a medical device or a part thereof to be in contact with a biogenic substance or a body tissue with the medical device material of the present invention, thereby attaching the medical device material of the present invention. As described, the medical device material of the present invention can be used as a surface treatment agent for a medical device or a part thereof, for example, as an antithrombogenic coating agent. Such an antithrombogenic coating agent using the medical device material of the present invention is one aspect of the present invention and the method of using the medical device material of the present invention as an antithrombogenic coating agent is also one aspect of the present invention.

A coating agent containing at least one of the polymer for a medical device of the first invention, the polymer for a medical device of the second invention and the polymer for a medical device of the third invention is also encompassed in the present invention. The coating agent of the present invention preferably contains the polymer for a medical device of the present invention (the total of the polymers if a plurality of polymers are contained) in an amount of, for example, 0.1 mass % or more and 90 mass % or less. The coating agent of the present invention is preferably used as, for example, a coating agent for a medical apparatus and an antithrombogenic coating agent.

The method for producing the polymer for a medical device of the present invention is a suitable method for producing a polymer for a medical device. A method for producing a medical device or a part thereof including the entire process from a step of producing a polymer in accordance with such a production method to a step of producing a medical device or a part thereof of the present invention using the polymer obtained, as described above; more specifically, a method for producing a medical device or a part thereof including a step of polymerizing a monomer component, which contains a glycerol group-containing monomer in which the content of a compound having two or more (meth)acryloyl groups in a single molecule relative to the glycerol group-containing monomer (100 mass %) is 0.3 mass % or less and an unsaturated monomer having a structure in which an organic group having a structure site having 4 or more carbon atoms continuously bound is bound to an ethylenically unsaturated group; and a step of attaching the polymer obtained in the polymerization step to at least a part of the portion of a medical device or a part thereof to be in contact with a biogenic substance or a body tissue, is one aspect of the present invention.

The medical device or a part thereof obtained by using the medical device material of the present invention and the antithrombogenic coating agent, more specifically, a medical device or a part thereof having at least part of the portion to be in contact with a biogenic substance or a body tissue constituted of the above medical device material and antithrombogenic coating agent is also one aspect of the present invention; and an antithrombogenic material and a cell culture medium obtained by using the medical device material of the present invention is also one aspect of the present invention.

In the medical device or a part thereof of the present invention, it is sufficient that at least a part of the device or the part to be in contact with a biogenic substance or a body tissue is constituted of the medical device material; preferably 50% or more of the area of the part to be in contact with a biogenic substance or a body tissue is covered with the medical device material, more preferably 80% or more of the area is covered; and most preferably the entire area of the part to be in contact with a biogenic substance or a body tissue is covered with the medical device material.

The medical device or a part thereof of the present invention can be used in any case (use) where it comes into contact with a biogenic substance and a body tissue. A preferred embodiment for the medical device or a part thereof of the present invention is the case where the device or a part thereof is used in contact with blood.

As a method for attaching the medical device material and antithrombogenic coating agent of the present invention to portions of medical devices to be in contact with a biogenic substance or body tissue, various methods can be used. Examples of the methods include a method of coating the surface of a medical device or a part thereof with the medical device material and the antithrombogenic coating agent; a method of binding the surface of a medical device and the medical device material or the antithrombogenic coating agent by graft polymerization with the help of an active energy ray such as radiation, an electron beam and ultraviolet rays; and a method of reacting a functional group on the surface of a medical device and the medical device material or the antithrombogenic coating agent to bind them.

In the case where the coating method is used, any one of the methods including coating, spraying and dipping may be employed for coating the surface of a medical device or a part thereof with the medical device material or the antithrombogenic coating agent. Note that, coating may be carried out by applying a composition essentially containing the monomer component serving as a material for a polymer for a medical device by e.g., coating, spraying or dipping, and thereafter, carrying out a polymerization reaction while heating or irradiating e.g., an active energy ray to form a layer of the medical device material or antithrombogenic coating agent of the present invention on the surface of the medical device or the material for a medical device.

A method for producing a medical device or a part thereof, comprising a step of attaching the medical device material of the present invention to the surface of a medical device or a part thereof is one aspect of the present invention.

The material for a medical device or a part thereof, to which the medical device material or antithrombogenic coating agent of the present invention to be attached, is not particularly limited. Any one of the materials may be used including polyethylene, polypropylene, polyvinyl chloride, polyvinylidene chloride, polyvinylidene fluoride, polytetrafluoroethylene, halogenated polyolefin, polyethylene terephthalate, polycarbonate, polyamide, an acrylic resin, polystyrene, a polyurethane resin, a silicone resin, polysulfone, polyether sulfone, cellulose and cellulose acetate. In addition, a metal, a ceramic and a composite thereof may be mentioned as an example. Alternatively, a base material may be constituted of a plurality of base substances. Examples of the metal include, but are not limited to, precious metals such as gold and silver; base metals such as copper, aluminum, tungsten, nickel, chromium and titanium; alloys of these metals and these metals whose surfaces are plated with gold. The metals may be used alone or in the form of an alloy with other metals or an oxide to give a functionality. In view of price and availability, nickel, copper and a metal containing each of these as a main component are preferably used. The main component herein refers to a component occupying 50 weight % or more of the material forming the base substance. The form of the base material is not particularly limited. For example, a molding, a fiber, a nonwoven cloth, a porous body, a particle, a film, a sheet, a tube, a hollow fiber or a powder may be used.

When the medical device material of the present invention is used as a cell culture medium, the medical device material may be directly used and may be applied onto a predetermined base material.

Examples of the base material that can be used include, but are not particularly limited to, a natural polymer such as cotton, hemp, agar, gelatin and collagen; and a synthetic polymer such as polyester, nylon, olefin, polyamide, polyurethane, polyacrylonitrile, poly (meth)acrylate, polyethylene, polypropylene, polyvinyl chloride, polyvinylidene chloride, polyvinylidene fluoride, polytetrafluoroethylene, halogenated polyolefin, polycarbonate, a polystyrene resin and a silicon resin. In addition, a metal, a ceramic and a composite thereof may be mentioned as an example. Alternatively, a base material may be constituted of a plurality of base substances. Examples of the metal include, but are not limited to, precious metals such as gold and silver; base metals such as copper, aluminum, tungsten, nickel, chromium and titanium; alloys of these metals and these metals whose surface is plated with gold. The metals may be used alone or in the form of an alloy with other metals or an oxide to give a functionality. In view of price and availability, nickel, copper and a metal containing each of these as a main component are preferably used. The main component herein refers to a component occupying 50 weight % or more of the material forming the base substance.

The form of the base material is not particularly limited. For example, a molding, a fiber, a nonwoven cloth, a porous body, a particle, a film, a sheet, a tube, a hollow fiber or a powder may be used.

The medical device material of the present invention can be applied to a member for an artificial body tissue such as an artificial blood vessel and an artificial organ; a member of a tool to be used in contact with a body tissue such as a blood filter, a catheter or a stent; and a member of a tool to be in contact with a living-body derived component (e.g., cells, blood) such as a cell culture medium, a member for a blood dialysis machine and a member for an examination tool for a blood or tissue.

More specifically, examples of the medical device or a part thereof according to the present invention include a tool to be in contact with a body tissue and a tool or a part thereof to be in contact with a living-body derived component (e.g., cells, blood).

More specifically, the medical device material in the present invention refers to a material for use in a medical device, a cell culture medium and an antithrombogenic material to be in contact with a body tissue and a living-body derived component (e.g., cells, blood).

EXAMPLES

Now, the present invention will be more specifically described by way of Examples; however, the present invention is not limited to these Examples. Note that, unless otherwise specified, "parts" refers to "parts by weight"; and "%" refers to "mass %".

GC measurement and determination of a weight-average molecular weight, number average molecular weight and the ratio of a component having a molecular weight of 5000 or less in Synthesis Examples, Examples and Comparative Examples, were carried out in accordance with the following methods.

<GC (Gas Chromatography)>

GC measurement was carried out by using GC-2010 (manufactured by Shimadzu Corporation) having a capillary column DB-17HT, L30 m×ID 0.25 mm, DF 0.15 mm.

A peak area was measured by connecting the left and right base lines with a straight line and specifying the area of the portion surrounded by the base line and the peak, as the peak area.

<Weight-Average Molecular Weight, Number Average Molecular Weight, the Ratio of a Component Having a Molecular Weight of 5000 or Less>

A polymer was dissolved and diluted with tetrahydrofuran. The solution obtained was passed through a filter of 0.45 μm in pore diameter (non-aqueous type Chromatodisk, manufactured by KURABO INDUSTRIES LTD.) and subjected to measurement by a gel permeation chromatographic (GPC) apparatus in the following conditions.

Apparatus: HLC-8320GPC (manufactured by Tosoh Corporation)
Elution solvent: tetrahydrofuran
Standard substance: standard polystyrene (manufactured by Tosoh Corporation)
Separation column: TSKgel SuperH5000, TSKgel SuperH4000, TSKgel SuperH3000 (manufactured by Tosoh Corporation)

Synthesis Example (1) Synthesis of GLMA (Glycerol Monoacrylate)

A reaction vessel having a stirrer placed therein was equipped with a gas inlet pipe, a thermometer, a cooling pipe and a distilling head connecting to a distillate receiver and charged with methyl acrylate (230 g) and 2,2-dimethyl-1,3-dioxolane-4-methanol (DOM) (70 g). The reaction solution was stirred while supplying an oxygen/nitrogen gas mixture (oxygen concentration 7 vol %) through the gas inlet pipe and heated in an oil bath (bath temperature 110° C.). After it was confirmed that the elution of water into the distillate ceased, titanium tetraisopropoxide (4.5 g) was added to the reaction vessel to initiate a transesterification reaction. While generating methanol was distilled off with methyl acrylate by azeotropic distillation, gas chromatographic (GC) analysis was carried out and the iPGLMA (isopyridine glyceryl acrylate)/DOM area ratio was monitored. After it was confirmed that the iPGLMA/DOM area ratio exceeded 9/1 in GC analysis seven hours from initiation of the reaction, the reaction was terminated and the reaction solution was cooled to room temperature. To the reaction solution, purified water (150 g), and ethyl acetate (300 g) as an extraction solvent, were added and stirred for 10 minutes. A precipitate of titanium oxide, which was produced by hydrolysis of the catalyst, was removed by suction filtration. The resultant filtrate was transferred to a separatory funnel to separate an organic layer and an aqueous layer. The organic layer was washed twice with purified water and then transferred to a rotary evaporator. The residual methyl acrylate and low-boiling point components were distilled off to obtain iPGLMA (96 g).

To an eggplant flask having a stirrer placed therein was equipped with a gas inlet pipe, purified water (160 ml) and iPGLMA (80 g) were added and dissolved. Thereafter, 35 g of a solid acid catalyst, Amberlyst 15J wet (manufactured by ORGANO CORPORATION), which was previously soaked in water and air-dried, was added. The reaction solution was stirred while supplying an oxygen/nitrogen gas mixture (oxygen concentration 7 vol %) through the gas inlet pipe and a deprotection reaction was initiated at room temperature. The GLMA/iPGLMA area ratio was monitored by GC analysis. After it was confirmed that the area ratio exceeded 99/1, the reaction was terminated in 4 hours. The solid acid catalyst was filtered off and the resultant filtrate was washed with n-hexane to remove unreacted iPGLMA. The aqueous layer was concentrated under reduced pressure to obtain a desired GLMA (53 g). The contents of crosslinkable impurities (compounds having two or more (meth)acryloyl groups in a single molecule) and chlorine in the resulting product were analyzed. Similarly, with respect to Blenmer GLM (commercially available glycerin monomethacrylate, manufactured by NOF Corporation), the content of crosslinkable impurities were analyzed by GC in the same manner. The content of chlorine was obtained by burning a sample at 900° C. in a combustion apparatus QF02, manufactured by Mitsubishi Chemical Corporation, allowing a 0.3% aqueous hydrogen peroxide solution (20 ml) to absorb the generating gas, and subjecting the absorption solution to ion chromatography for determination of the content of chlorine. The results are shown in Table 1.

Note that, GLMA was synthesized in the same manner as above except that "acidic zeolite HSZ-609HOA (manufactured by Tosoh Corporation)" was used in place of "solid acid catalyst Amberlyst 153 wet". The contents of crosslinkable impurities and chlorine were analyzed. As a result, the content of the crosslinkable impurities was 0.15 wt % and the content of chlorine was 0.01 wt % or less.

TABLE 1

|  | Crosslinkable impurities (wt %) | Chlorine (wt %) |
|---|---|---|
| GLMA | 0.19 | 0.01 or less |
| Blenmer GLM | 0.54 | 0.18 |

(2) Synthesis of GLMM (Glycerol Monomethacrylate)

A desired GLMM was obtained in the same manner as in Synthesis Example (1) except that methyl methacrylate was used in place of methyl acrylate.

(3) Synthesis of AOMA-GL (Glycerol Allyloxymethacrylate)

A reaction vessel having a stirrer placed therein was equipped with a gas inlet pipe, a thermometer, a cooling pipe and a distilling head connecting to a distillate receiver and charged with 2,2-dimethyl-1,3-dioxolane-4-methanol (120 g), methyl α-allyloxymethylacrylate (AOMA-M) (70 g) and cyclohexane (120 g). The reaction solution was stirred while supplying an oxygen/nitrogen gas mixture (oxygen concentration 7%) through the gas inlet pipe and heated in an oil bath (bath temperature 100° C.). After it was confirmed that the elution of water into the distillate ceased, titanium tetraisopropoxide (3.0 g) was added to the reaction vessel to initiate a transesterification reaction. While generating methanol was distilled off with cyclohexane by azeotropic distillation, gas chromatographic (GC) analysis was carried out and the isopropylidene glyceryl α-allyloxymethacrylate (AOMA-iPGL)/AOMA-M area ratio was monitored. Titanium tetraisopropoxide (1.5 g) and cyclohexane (25 g) were added at intervals of 3 hours until the AOMA-iPGL/AOMA-M area ratio exceeded 9/1 in GC analysis. After cyclohexane was removed by reducing pressure, the reaction solution was cooled to room temperature. After ion-exchange water (120 g), and n-hexane as an extraction solvent, were added and stirred, titanium oxide, which is a hydrolysate of the catalyst, was removed by filtration. The filtrate was transferred to a separatory funnel to separate an organic layer and an aqueous layer. Then, the organic layer was washed by adding ion-exchange water to the organic layer. The residual 2,2-dimethyl-1,3-dioxolane-4-methanol was allowed to migrate into the aqueous layer. The resultant organic layer was heated under reduced pressure to distill off n-hexane to obtain AOMA-iPGL (100 g). To the obtained AOMA-iPGL (50 g), ion-exchange water (70 g) and a solid acid catalyst, 15 g of Amberlyst 15J WET (manufactured by ORGANO CORPORATION) were added. The reaction solution was stirred for 24 hours at room temperature while supplying an oxygen/nitrogen gas mixture (oxygen concentration 7 vol %), filtered, and heated under reduced pressure to distill off water and by-products. In this manner, AOMA-GL (39 g) was obtained.

(4) Synthesis of MG-2GL (Diglyceryl Methyleneglutarate)

A reaction vessel having a stirrer placed therein was equipped with a gas inlet pipe, a thermometer and a dean stark apparatus equipped with a reflux column and a condenser, and charged with dimethyl methyleneglutarate (MG-2M) (30 g), 2,2-dimethyl-1,3-dioxolane-4-methanol (DOM) (120 g) and dibutyltin oxide (1.8 g). The reaction solution was stirred while supplying an oxygen/nitrogen gas mixture (oxygen concentration 7 vol %) through the gas inlet pipe and heated in an oil bath (bath temperature 130° C.) and a transesterification reaction was initiated under reduced pressure of 10 kPa. While distilling off generating methanol, reduction of MG-2M was monitored by gas chromatographic (GC) analysis. The reaction was terminated in 12 hours. The reaction solution was cooed to room temperature and saturated saline (75 g), and ethyl acetate (150 g) as an extraction solvent, were added to the reaction solution. The reaction solution was transferred to a separatory funnel to separate an organic layer and an aqueous layer. After the organic layer was washed a plurality of times with water (75 g) to remove excessive starting alcohol and a light boiling fraction was distilled off under reduced pressure to obtain 42 g of diisopyridenegryceryl methyleneglutarate (MG-2iPGL).

To a flask equipped with a gas inlet pipe, methanol (300 ml) and MG-2iPGL (30 g) were added and dissolved. Thereafter, 50 g of solid acid catalyst Amberlyst 15JWet, which was previously soaked in water and air-dried, was added. The reaction solution was stirred by a paddle blade while supplying an oxygen/nitrogen gas mixture (oxygen concentration 7 vol %) through the gas inlet pipe to initiate a deprotection reaction at room temperature. Thin-layer chromatography (developing solvent; ethyl acetate) was carried out. Absence of a spot of MG-2iPGL and presence of spots of an intermediate and a target substance were confirmed and the reaction was terminated in 24 hours. The solid acid catalyst was filtered off and the obtained filtrate was washed with n-hexane to remove unreacted MG-2iPGL, concentrated under reduced pressure. The product thus obtained was isolated by a silica gel column (mobile phase: methanol/ethyl acetate) to obtain 10 g of a desired diglyceryl methyleneglutarate (MG-2GL) as a light yellow transparent liquid.

Example (1) Production of PGB37

A reaction vessel having a stirrer placed therein was equipped with a gas inlet pipe, a thermometer and a cooling pipe and charged with GLMA (1.5 g) and butyl acrylate (BA) (3.5 g) as monomers, methyl ethyl ketone (5.0 g) as a solvent and an azo-based radical polymerization initiator (0.025 g) (trade name: V-601, manufactured by Wako Pure Chemical Industries Ltd.). The reaction solution was stirred and heated while supplying nitrogen gas. Polymerization was carried out at an internal temperature of 80° C. and carried out for 3 hours.

The obtained reaction solution was diluted with acetone, poured in a large amount of n-hexane while stirring and allowed to reprecipitate. The precipitate was dried by a vacuum dryer at 80° C. for 3 hours under reduced pressure to obtain a solid polymer (PGB37). The obtained polymer had a weight-average molecular weight of 153,000. The content of the component having a molecular weight of 5,000 or less was 0.5% or less. The polymer was dissolved in methanol to obtain a 1% solution. No insoluble matter was visually observed in the solution. The solution was filtered with a 0.45 μm filter (non-aqueous type Chromate disk manufactured by KURABO INDUSTRIES LTD.). The weight of the insoluble matter was obtained based on a weight increase of the filter; however, no polymer agglomerate remained on the filter and a weight change of the filter was 0.1% or less.

(2) Production of PGB 46

A solid polymer (PGB46) was obtained in the same manner as in Example (1) except that GLMA (2.0 g) and butyl acrylate (BA) (3.0 g) as monomers were used. The resulting polymer had a weight-average molecular weight of 134,000, a molecular weight distribution of 2.9, and the content of a component having a molecular weight of 5000 or less was 0.5% or less. The polymer was dissolved in methanol to obtain a 1% solution. No insoluble matter was visually observed in the solution. The solution was filtered with a 0.45 μm filter and the weight of the insoluble matter was obtained based on a weight increase of the filter; however, no polymer agglomerate remained on the filter and a weight change of the filter was 0.1% or less.

(3) Production of PGB55

A solid polymer (PGB55) was obtained in the same manner as in Example (1) except that GLMA (2.5 g) and butyl acrylate (BA) (2.5 g) were used as monomers. The obtained polymer had a weight-average molecular weight of 75,000 and the content of a component having a molecular weight of 5000 or less was 0.5% or less. The polymer was dissolved in methanol to obtain a 1% solution. No insoluble matter was visually observed in the solution. The solution was filtered with a 0.45 μm filter (non-aqueous type Chromate disk manufactured by KURABO INDUSTRIES LTD.) and the weight of the insoluble matter was obtained based on a weight increase of the filter; however, no polymer agglomerate remained on the filter and a weight change of the filter was 0.1% or less.

(4) Production of PGmB46

A solid polymer (PGmB46) was obtained in the same manner as in Example (1) except that GLMM (2.0 g) and butyl acrylate (BA) (3.0 g) were used as monomers. The obtained polymer had a weight-average molecular weight of 218,000 and the content of a component having a molecular weight of 5000 or less was 0.5% or less. The polymer was dissolved in methanol to obtain a 1% solution. No insoluble matter was visually observed in the solution. The solution was filtered with a 0.45 µm filter (non-aqueous type Chromate disk manufactured by KURABO INDUSTRIES LTD.) and the weight of the insoluble matter was obtained based on a weight increase of the filter; however, no polymer agglomerate remained on the filter and a weight change of the filter was 0.1% or less.

(5) Production of PAgB55

A solid polymer (PAgB55) was obtained in the same manner as in Example (1) except that AOMA-GL (2.5 g) and butyl acrylate (BA) (2.5 g) were used as monomers. The obtained polymer had a weight-average molecular weight of 300,000 and the content of a component having a molecular weight of 5000 or less was 0.5% or less. The polymer was dissolved in methanol to obtain a 1% solution. No insoluble matter was visually observed in the solution. The solution was filtered with a 0.45 µm filter (non-aqueous type Chromate disk manufactured by KURABO INDUSTRIES LTD.) and the weight of the insoluble matter was obtained based on a weight increase of the filter; however, no polymer agglomerate remained on the filter and a weight change of the filter was 0.1% or less.

(6) Production of PM2gB46

A reaction vessel having a stirrer placed therein was equipped with a gas inlet pipe, a thermometer and a cooling pipe and charged with MG-2GL (2.0 g), butyl acrylate (BA) (3.0 g) as monomers, methanol (5.0 g) as a solvent and an azo-based radical polymerization initiator (0.025 g) (trade name: V-65, manufactured by Wako Pure Chemical Industries Ltd.). The reaction solution was stirred and heated while supplying nitrogen gas. Polymerization was initiated at an internal temperature of 50° C. and carried out for 12 hours.

The obtained reaction solution was diluted with acetone, poured in a large amount of n-hexane while stirring, and allowed to reprecipitate to obtain a solid polymer (PM2gB46). The obtained polymer had a weight-average molecular weight of 346,000 and the content of a component having a molecular weight of 5000 or less was 0.5% or less. The polymer was dissolved in methanol to obtain a 1% solution. No insoluble matter was visually observed in the solution. The solution was filtered with a 0.45 µm filter (non-aqueous type Chromate disk manufactured by KURABO INDUSTRIES LTD.) and the weight of the insoluble matter was obtained based on a weight increase of the filter; however, no polymer agglomerate remained on the filter and a weight change of the filter was 0.1% or less.

Reference Example 1

(1) Synthesis of GLMM (Commercially Available Product)/BA Copolymer

Polymerization was carried out in the same manner as Example (2) except that Blenmer GLM described in Table 1 was used as the monomer in place of GLMA. As a result, the viscosity of the reaction solution increased in the middle of polymerization and gelatinization was observed.

Comparative Example (1) Production of PGS46

A reaction vessel having a stirrer placed therein was equipped with a gas inlet pipe, a thermometer and a cooling pipe and charged with GLMA (2.0 g), styrene (ST) (3.0 g) as monomers, dioxane (5.0 g) as a solvent and an organic peroxide (0.01 g) (trade name: Luperox 575, manufactured by Kayaku Akzo Corporation). The reaction solution was stirred and heated while supplying nitrogen gas. Polymerization was initiated at an internal temperature of 90° C. and carried out for 8 hours.

The obtained reaction solution was diluted with acetone, poured in a large amount of n-hexane while stirring and allowed to reprecipitate. The precipitate was dried by a vacuum dryer at 80° C. for 3 hours under reduced pressure to obtain a solid polymer (PGS46). The obtained polymer had a weight-average molecular weight of 74,000 and the content of a component having a molecular weight of 5000 or less was 0.5% or less. The polymer was dissolved in methanol to obtain a 1% solution. No insoluble matter was visually observed in the solution. The solution was filtered with a 0.45 µm filter (non-aqueous type Chromate disk manufactured by KURABO INDUSTRIES LTD.) and the weight of the insoluble matter was obtained based on a weight increase of the filter; however, no polymer agglomerate remained on the filter and a weight change of the filter was 0.1% or less.

(2) Production of PGBm46

A reaction vessel having a stirrer placed therein was equipped with a gas inlet pipe, a thermometer and a cooling pipe and charged with GLMA (2.0 g), butyl methacrylate (BMA) (3.0 g) as monomers, dioxane (5.0 g) as a solvent and an organic peroxide (0.01 g) (trade name: Luperox 575, manufactured by Kayaku Akzo Corporation) were added. The reaction solution was stirred and heated while supplying nitrogen gas. Polymerization was initiated at an internal temperature of 90° C. and carried out for 8 hours.

The obtained reaction solution was diluted with acetone, poured in a large amount of n-hexane while stirring and allowed to reprecipitate. The precipitate was dried by a vacuum dryer at 80° C. for 3 hours under reduced pressure to obtain a solid polymer (PGBm46). The obtained polymer had a weight-average molecular weight of 218,000 and the content of a component having a molecular weight of 5000 or less was 0.5% or less. The polymer was dissolved in methanol to obtain a 1% solution. No insoluble matter was visually observed in the solution. The solution was filtered with a 0.45 µm filter (non-aqueous type Chromate disk manufactured by KURABO INDUSTRIES LTD.) and the weight of the insoluble matter was obtained based on a weight increase of the filter; however, no polymer agglomerate remained on the filter and a weight change of the filter was 0.1% or less.

(3) Production of PMEA

A reaction vessel equipped with a stirring blade, a gas inlet pipe, a thermometer and a cooling pipe, was charged with methoxyethyl acrylate (MEA) (20.0 g) as a monomer and methyl ethyl ketone (30.0 g) as a solvent. The reaction solution was stirred and heated while supplying nitrogen gas. After confirming that the internal temperature was stabilized at 70° C., a solution obtained by dissolving an azo-based radical polymerization initiator (0.02 g) (trade name: V-601, manufactured by Wako Pure Chemical Industries Ltd.) in methyl ethyl ketone (0.5 g) was added to initiate polymerization. While the internal temperature was controlled to fall within the range of 69° C. to 71° C., a solution obtained by dissolving 0.02 g of V-601 in methyl ethyl ketone (0.5 g) was added every 4 hour and finally a reaction was carried out for 8 hours.

The obtained reaction solution was diluted with acetone, poured in a large amount of ion-exchange water while stirring and allowed to reprecipitate to obtain a solid polymer (PMEA). The obtained polymer had a weight-average molecular weight of 130,000 and the content of a component having a molecular weight of 5000 or less was 0.5% or less.

Polymers produced in Examples (1) to (6), Comparative Examples (1) to (3), a biocompatible polymer (phosphocholine polymer, trade name: Lipidure-CM5206, manufactured by NOF Corporation) and a PET film were subjected to measurement of glass-transition temperature, glass-transition temperature of a polymer containing water and the amount of a glycerol group according to the following methods. Biocompatibility (antithrombogenicity) was evaluated based on a platelet adhesion test and contact angle. Furthermore, the polymer produced in Example (2) and PMEA were subjected to a substrate adhesion test according to the following method. The results are shown in Table 2. Table 2 also shows the molecular weight, molecular weight distribution and the content of a component having a molecular weight of 5000 or less and the amount of insoluble matter of each polymer.

<Measurement Method of Tg>

Measurement was carried out in accordance with JIS K7121 by the following differential scanning calorimeter in the following conditions. The glass-transition temperature (Tg) was obtained by a middle-point method.

Apparatus: DSC 3100 (manufactured by Bruker AXS)
Temperature increasing rate: 10° C./minute
Nitrogen flow rate: 50 ml/minute <Measurement of Tg of Polymer Containing Water>

A polymer and water same amount as the polymer were added in a pressure-resistant aluminum pan. The pan was closed airtight and allowed to stand still for a day and night. The temperature was increased from −100° C. to 40° C. at a rate of 5° C./rain, and measurement was carried out.

<Content of Glycerol Group>

The composition of a polymer was calculated based on the reaction ratio of a monomer by GC (gas chromatography).

<Platelet Adhesion Test>

Antithrombogenicity was evaluated by a platelet adhesion test. A 0.2% methanol solution of each material to be tested was prepared, applied onto a PET film by spin coating and dried to obtain a sample. On the sample, fresh human platelet-rich plasma (0.2 mL) treated with sodium citrate so as not to coagulate was added dropwise by a pipette and allowed to stand still at 37° C. for 60 minutes. Subsequently, the PET film was rinsed with a phosphate buffer solution and fixed with glutaraldehyde. A base substance was observed by a scanning electron microscope and the number of platelets adhered in an area of $1\times10^4$ $\mu m^2$ was counted. The platelets were classified depending upon the degree of a morphological change into three types: Type 1 (normal), Type 2 (formation of pseudopod) and Type 3 (elongation). MS (morphological score) was defined as follows and calculated. Based on the MS obtained by calculation, biocompatibility was evaluated on a scale of 5 stages.

$$MS = n_1 \times 1 + n_2 \times 2 + n_3 \times 3$$

where $n_1$ represents the count of Type-1 platelets; $n_2$ represents the count of Type-2 platelets; and $n_3$ represents the count of Type-3 platelets A: MS=0 or more and less than 100
B: MS=100 or more and less than 300
C: MS=300 or more and less than 600
D: MS=600 or more and less than 1000
E: MS=1000 or more Note that, smaller MS means that platelets less likely to adhere and represents excellent biocompatibility. MS of the PET film as a control was evaluated as E.

<Contact Angle (Bubble Method)>

Each of the sample films was fixed onto a stage by means of a double-sided tape attached to the back surface of the sample film. An air bubble of 1.5 μl was allowed to be in contact with the surface of the film in water and the contact angle was measured by a contact-angle goniometer.

<Substrate Adhesion Test>

A 1% methyl ethyl ketone solution of each of the materials to be tested was prepared, applied onto a substrate by a bar coater and dried to form a coating film of about 3 μm in thickness on the substrate. Each substrate was soaked in ion-exchange water overnight. A change of appearance was visually observed and the condition of the surface was observed by a microscope.

TABLE 2

| | | Example | | | | | |
|---|---|---|---|---|---|---|---|
| | | (1) | (2) | (3) | (4) | (5) | (6) |
| Co-polymer composition (wt %) | GLMA | 30 | 40 | 50 | — | — | — |
| | GLMM | — | — | — | 40 | — | — |
| | AOMA-GL | — | — | — | — | 50 | — |
| | MG-2GL | — | — | — | — | — | 40 |
| | BA | 70 | 60 | 50 | 60 | 50 | 60 |
| | BMA | — | — | — | — | — | — |
| | ST | — | — | — | — | — | — |
| Copolymer name | | PGB37 | PGB46 | PGB55 | PGmB46 | PAgB55 | PM2gB46 |
| Tg (° C.) | | −44 | −40 | −36 | −25 | −13 | −22 |
| Tg of polymer containing water (° C.) | | −52 | −50 | −58 | −40 | −35 | −42 |
| Glycerol group (mmol/g) | | 2.05 | 2.74 | 3.42 | 2.5 | 2.31 | 2.74 |
| Platelet adhesion test (MS) | | A | A | A | A | A | A |
| Contact angle (wet) | | 166.6 | 165.6 | 167.2 | 164.5 | 165.5 | 166 |
| Molecular weight | weight-average | 153,000 | 134,000 | 75,000 | 218,000 | 300,000 | 346,000 |
| | number-average | 58,000 | 46,000 | 28,000 | 82,000 | 67,000 | 78,000 |
| | distribution | 2.6 | 2.9 | 2.7 | 2.7 | 4.5 | 4.5 |

TABLE 2-continued

| | | | | | | | |
|---|---|---|---|---|---|---|---|
| Content of a component having a molecular weight of 5000 or less | | 0.5% or less | 0.5% or less | 0.5% or less | 0.5% or less | 0.5% or less | 0.5% or less |
| Amount of insoluble matter | | 0.1% or less | 0.1% or less | 0.1% or less | 0.1% or less | 0.1% or less | 0.1% or less |
| Substrate adhesion | glass | — | No change | — | — | — | — |
| 37° C. water immersion *24 hr | polypropylene | — | No change | — | — | — | — |

| | | Comparative Example | | | | |
|---|---|---|---|---|---|---|
| | | (1) | (2) | (3) | (4) | (5) |
| Co-polymer composition (wt %) | GLMA | 40 | 40 | — | — | — |
| | GLMM | — | — | | | |
| | AOMA-GL | — | — | | | |
| | MG-2GL | — | — | | | |
| | BA | — | — | | | |
| | BMA | — | 60 | | | |
| | ST | 60 | — | | | |
| Copolymer name | | PGS46 | PGBm46 | PMEA | CM5206 | PET film |
| Tg (° C.) | | 79 | 25 | −40 | 64 | 60 |
| Tg of polymer containing water (° C.) | | 40 or more | −10 to −20 | — | — | — |
| Glycerol group (mmol/g) | | 2.74 | 2.74 | 0 | 0 | 0 |
| Platelet adhesion test (MS) | | D | D | A | A | E |
| Contact angle (wet) | | 143.3 | 123 | 155.0 | 168.0 | 120.0 |
| Molecular weight | weight-average | 74,000 | 218,000 | 130,000 | — | — |
| | number-average | 24,000 | 53,000 | 45,000 | — | — |
| | distribution | 3.1 | 4.1 | 2.9 | — | — |
| Content of a component having a molecular weight of 5000 or less | | 0.5% or less | 0.5% or less | 0.5% or less | — | — |
| Amount of insoluble matter | | 0.1% or less | 0.1% or less | 0.1% or less | — | — |
| Substrate adhesion | glass | — | — | Many holes | — | — |
| 37° C. water immersion *24 hr | polypropylene | — | — | Many holes | — | — |

PMEA and CM5206 used in Comparative Examples (3) and (4), are commonly known as the materials having excellent biocompatibility. In the platelet adhesion test, the number of platelets adhered to the GLMA/BA copolymer (PGB46) of Example (2) was equal to and lower than that to PMEA and CM5206, and thus PGB46 was confirmed to have excellent biocompatibility. Since the number of platelets adhered to PET used as a negative control is large, it is guaranteed that right evaluation is made by this test method.

In the substrate adhesion test, when PMEA, which has poor adhesiveness to a substrate, was soaked in water, the coating film was swollen and repelled the substrate, with the result that eye holes were formed in the coating film and the substrate. Due to the small holes, the appearance looked white and turbid. In contrast, a change was neither visually nor microscopically observed in PGB46. From this, it was confirmed that adhesion of the coating film to a substrate is excellent.

From the results shown in Table 2, it was demonstrated that the polymer satisfying predetermined requirements of the present invention is excellent in antithrombogenicity and suitable as a medical device material.

The invention claimed is:

1. A polymer having a structural unit derived from a glycerol group-containing monomer, and a structural unit derived from an unsaturated monomer having a structure in which an organic group having a structure site having 4 or more continuously-bound carbon atoms is bound to an ethylenically unsaturated group; and
   satisfying a glass-transition temperature of −5° C. or less and/or a glass-transition temperature of −25° C. or less at a saturated water content.

2. A polymer having a glycerol group in a ratio of 1 mmol or more per 1 g of polymer and satisfying a glass-transition temperature of −5° C. or less and/or a glass-transition temperature of −25° C. or less at a saturated water content.

3. The polymer according to claim 1,
   wherein the polymer has a structural unit derived from glycerol (meth)acrylate or a derivative thereof.

4. The polymer according to claim 1,
   wherein the polymer has a weight-average molecular weight of 1,000 to 10,000,000.

5. The polymer according to claim 1,
   wherein the polymer contains insoluble matter in a content of 10 mass % or less relative to the mass of the polymer.

6. A medical device material, containing the polymer according to claim 1.

7. A method for using the polymer according to claim 1 as a medical device material.

8. An antithrombogenic coating agent containing the polymer according to claim 1.

9. A method for using the medical device material according to claim 6 as an antithrombogenic coating agent.

10. A medical device or a part thereof having at least a part to be in contact with a biogenic substance or a body tissue is constituted of the medical device material according to claim 6.

11. A method for producing a polymer, comprising
a step of polymerizing a monomer component containing a glycerol group-containing monomer and an unsaturated monomer having a structure in which an organic group having a structure site having 4 or more carbon atoms continuously bound is bound to an ethylenically unsaturated group,
wherein the glycerol group-containing monomer contains a compound having two or more (meth)acryloyl groups in a single molecule in a content of 0.3 mass % or less relative to 100 mass % of the glycerol group-containing monomer.

12. A method for producing a medical device or a part thereof, comprising a step of attaching the medical device material according to claim 6 to the surface of a medical device or a part thereof.

13. The polymer according to claim 2,
wherein the polymer has a structural unit derived from glycerol (meth)acrylate or a derivative thereof.

14. The polymer according to claim 2,
wherein the polymer has a weight-average molecular weight of 1,000 to 10,000,000.

15. The polymer according to claim 2,
wherein the polymer contains insoluble matter in a content of 10 mass % or less relative to the mass of the polymer.

16. A medical device material, containing the polymer according to claim 2.

17. A method for using the polymer according to claim 2 as a medical device material.

18. An antithrombogenic coating agent containing the polymer according to claim 2.

19. The polymer according to claim 1, wherein the ratio of the structural unit derived from a glycerol group-containing monomer relative to all structural units (100 mass %) contained in the polymer is 20 to 90 mass %.

20. The polymer according to claim 1, wherein the ratio of the structural unit derived from an unsaturated monomer having a structure in which an organic group having a structure site having 4 or more continuously-bound carbon atoms is bound to an ethylenically unsaturated group relative to all structural units (100 mass %) contained in the polymer is 10 to 70 mass %.

* * * * *